United States Patent
Morazzoni et al.

(10) Patent No.: US 11,026,984 B2
(45) Date of Patent: Jun. 8, 2021

(54) USE OF ISOTHIOCYANATE DERIVATIVES AS MODULATORS OF PERIPHERAL AND NEUROPATHIC PAIN

(71) Applicant: Indena S.P.A., Milan (IT)

(72) Inventors: Paolo Morazzoni, Milan (IT); Renato Iori, Bologna (IT)

(73) Assignee: Indena S.P.A., Milan (IT)

( * ) Notice: Subject to any disclaimer, the term of this patent is extended or adjusted under 35 U.S.C. 154(b) by 46 days.

(21) Appl. No.: 15/564,748

(22) PCT Filed: Mar. 30, 2016

(86) PCT No.: PCT/EP2016/056864
§ 371 (c)(1),
(2) Date: Oct. 6, 2017

(87) PCT Pub. No.: WO2016/162246
PCT Pub. Date: Oct. 13, 2016

(65) Prior Publication Data
US 2018/0104293 A1    Apr. 19, 2018

(30) Foreign Application Priority Data

Apr. 10, 2015  (EP) .................... 15163185

(51) Int. Cl.
| | |
|---|---|
| *A61K 36/185* | (2006.01) |
| *A61K 31/7024* | (2006.01) |
| *A61K 31/26* | (2006.01) |
| *A61P 25/02* | (2006.01) |
| *A61P 25/00* | (2006.01) |
| *A61K 31/7034* | (2006.01) |

(52) U.S. Cl.
CPC ............ *A61K 36/185* (2013.01); *A61K 31/26* (2013.01); *A61K 31/7024* (2013.01); *A61K 31/7034* (2013.01); *A61P 25/00* (2018.01); *A61P 25/02* (2018.01)

(58) Field of Classification Search
None
See application file for complete search history.

(56) References Cited

U.S. PATENT DOCUMENTS

| | | | | |
|---|---|---|---|---|
| 6,075,053 | A | * | 6/2000 | Hausheer ............ A61K 31/185 514/578 |
| 8,772,251 | B2 | * | 7/2014 | Morazzoni ............ A61K 31/26 514/25 |
| 2010/0015085 | A1 | | 1/2010 | Konstantopoulos et al. |
| 2011/0053870 | A1 | * | 3/2011 | Morazzoni ............ A61K 31/26 514/24 |

FOREIGN PATENT DOCUMENTS

| | | | | |
|---|---|---|---|---|
| EP | 2080516 | A1 | * 7/2009 | ............ A61K 31/26 |
| EP | 2080516 | A1 | 7/2009 | |
| EP | 2292237 | A1 | 3/2011 | |

OTHER PUBLICATIONS

Website document entitled: "Oxaliplatin-Chemotherapy Drugs-Chemocare" (available at http://www.chemocare.com/chemotherapy/drug-info/oxaliplatin.aspx). Web archived to Oct. 10, 2012. (Year: 2012).*
Seretny et al. (2014) Pain 155: 2461-2470. (Year: 2014).*
Cerososimo (2005) Ann. Pharmacother. 39:128-135. (Year: 2005).*
International Preliminary Report on Patentability of PCT/EP2016/056864 dated Apr. 13, 2017.
Search Report and Written Opinion of PCT/EP2016/056864 dated May 18, 2016.

* cited by examiner

*Primary Examiner* — Russell G Fiebig
(74) *Attorney, Agent, or Firm* — Silvia Salvadori, P.C.; Silvia Salvadori

(57) ABSTRACT

The present invention relates to the use of glucomoringin (GMG) and of the corresponding isothiocyanate derivative glucomoringin des-thioglucoside (GMG-ITC) as modulators of peripheral pain with specific reference to that linked with diabetic peripheral neuropathy and chemotherapy-induced neuropathy.

3 Claims, 1 Drawing Sheet

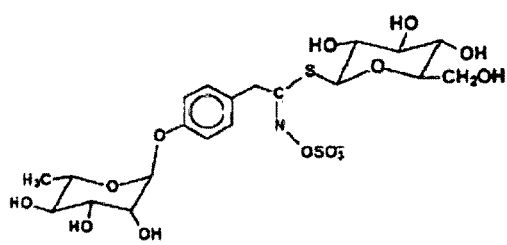
GMG
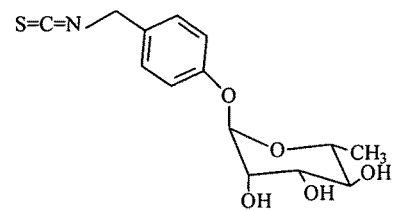
GMG-ITC

USE OF ISOTHIOCYANATE DERIVATIVES AS MODULATORS OF PERIPHERAL AND NEUROPATHIC PAIN

This application is a U.S. national stage of PCT/EP2016/056864 filed on 30 Mar. 2016, which claims priority to and the benefit of European Application No. 15163185.0 filed on 10 Apr. 2015, the contents of which are incorporated herein by reference in their entireties.

SUMMARY OF THE INVENTION

The present invention relates to the use of glucomoringin (GMG) and of the corresponding isothiocyanate derivative glucomoringin des-thioglucoside (GMG-ITC) as modulators of peripheral pain with specific reference to that linked with diabetic peripheral neuropathy and chemotherapy-induced neuropathy.

STATE OF THE ART

Diabetic peripheral neuropathy and chemotherapy-induced neuropathy are two conditions directly linked with generation of peripheral pain (Galuppo M., et al. Molecules 19, 2877-2895, 2014; Argyriou A. A. et al. Cancer Management and Research 6, 135-147, 2014). Pain is one of the first manifestations of inflammation, but other possible causes such as traumatic events, burns, post-operative or disease-related pain can be at its origin. Pain can be categorized as: nociceptive pain, a protective sensation associated as a reaction to a potentially harmful noxious stimuli; inflammatory pain, linked to tissue damage and infiltration of immune cells; pathological pain, as a damage to the peripheral or central nervous system (neuropathic) or as an altered alerting/response leading to an uncontrolled sensation of pain (dysfunctional). Chronic pain (longer than 6 months), and in particular neuropathic pain, are difficult to treat due to their severity and resistance to simple analgesics and are common features in many pathologies, such as diabetes, multiple sclerosis, Guillain-Barrè syndrome and Parkinson's disease characterized by peripheral nerve fibers that mainly due to demyelinization transmit abnormal painful sensations including hyperalgesia and allodynia. A peripheral neuropathy leading to pain is also associated with the clinical use of cancer chemotherapy. Chemotherapy drugs currently used to treat cancer (taxanes, cisplatin, oxaliplatin, epothilones, bortezomid, vincristine and others), in fact, can be neurotoxic by either exerting a direct noxious effect on the brain or the peripheral nerves. Depending on its severity, chemotherapy-induced neuropathy mainly linked to pain generation can be dose-limiting and may also markedly compromise quality of life of patients. Symptoms usually improve or resolve within 3 months after discontinuation of treatment, whereas severe symptoms may persist for a long period.

Therapeutic agents usually employed for chronic peripheral and neuropathic pain include off-label utilization of amitriptyline, glutamine, low-dose oral prednisone. More recently, gabapentin, duloxetine alone or in combination with pregabalin have provided additional measures in reducing pain, myalgia and arthralgia. In addition, several neuroprotective agents including amifostine, acetyl-L-carnitine and vitamin E have demonstrated some promising results but their routine use is not recommended in current clinical practice.

Despite of this list of products, a real unique treatment designed to relieve and counteract chronic peripheral and neuropathic pain has not been found to date and pharmacological researches are still looking for active products even considering natural and botanical derivatives. In this light, some plants containing phenolic compounds, cannabinoids, alkaloids and vanilloids have already been investigated with some success, leading to the development of oral and topical formulations such as Sativex (containing a standardized extract of *Cannabis sativa*) and Qutenza (patches containing capsaicin).

Glucomoringin (4-(α-L-rhamnosyloxy)-benzyl glucosinolate; GMG) is an uncommon member of the glucosinolates (GLs) family and presents a unique characteristic consisting in a second saccharidic residue in its side chain. Its structure is depicted in FIGURE along with that of the corresponding des-thioglucoside isothiocyanate (4-(α-L-rhamnosyloxy)-benzyl isothiocyanate; glucomoringin-des-thioglucoside; GMG-ITC) which is formed by bioactivation of GMG with the enzyme myrosinase.

GMG is a typical secondary metabolite present in vegetables belonging to the genus Moringaceae that consists of 14 species, among which *Moringa oleifera* is the most widely distributed. *Moringa oleifera* L. (horseradish tree) is a pan-tropical species also known with the following different names in relationship to the geographical area: benzolive, drumstick tree, kelor, marango, mionge, mulangay, saijhan and saijna (Fahey J. W. et al. Trees of Life Journal 2005 1:5; Mahmood K. T. J. Pharm. Sci &Res. 2, 775, 2010). *Moringa oleifera* is the most widely cultivated species of a monogenetic family, the Moringaceae that is native of the sub-Himalayan tracts of India, Pakistan, Bangladesh and Afghanistan. The plant was already utilized by the ancient Romans, Greeks and Egyptians; all parts of the tree are edible and in more modern era have long been consumed by humans. *Moringa* trees have been used to fight malnutrition, in particular among infants. More recently, attention has also focused on a modern confirmation of traditionally described potential health benefit deriving from utilization of both oral and topical preparation based on *Moringa oleifera* derivatives. The medical value of the seeds and other part of the plant have long been recognized in folk medicine (Longo P L (2001). Plasma cell disorders. In Braunwald E, Kasper D, Faucci A. eds Harrison's principles of internal medicine, 15th edn, vol. 1:727-33). A long list of traditional medicine references on the plant are available which include effects such as: antibiotic, antitrypanosomal, hypotensive, antispasmodic, antiulcer, hypocholesterolemic, hypoglycemic. However, most of these effects in humans are not supported by controlled studies and are generally observed through the usage of non-standardized derivatives of the plant.

GMG-ITC has been shown to exhibit a broad biological activity and it was also shown to exert an effective antitumor promoting activity (Guevara A P et al, Mutation Research, 440, 181-188, 1999) and in counteracting the inflammatory response (Galuppo M et al, Fitoterapia, 95, 160-174, 2014).

The use of GMG and of GMG-ITC for the treatment of myeloma is described in WO2009/089889 A1.

BRIEF DESCRIPTION OF THE FIGURE

FIGURE: Structure of glucomoringin (GMG) and of glucomoringin des-thioglucoside (GMG-ITC).

DESCRIPTION OF THE INVENTION

It has now surprisingly been found that GMG, its des-thio-glucoside GMG-ITC, or an extract of *Moringa oleifera* seeds containing GMG and/or GMG-ITC are endowed with a remarkable effect in modulating peripheral neuropathic pain in in vivo experimental models of diabetic animals and chemotherapy-induced neuropathy.

The object of the present invention is therefore GMG, GMG-ITC, or an extract of *Moringa oleifera* seeds containing GMG and/or GMG-ITC, for the treatment of peripheral neuropathic pain and chemotherapy-induced neuropathy.

In a preferred embodiment, the invention relates to isolated GMG or to an extract of *Moringa oleifera* seeds containing GMG, for the treatment of peripheral neuropathic pain and chemotherapy-induced neuropathy.

An extract of *Moringa oleifera* seeds containing GMT and GMT-ITC can be obtained treating the de-fatted flour of the pealed seeds with a 70% ethanol aqueous solution at about 75-80° C. or with water at 80-90° C. The water extract is then freeze-dried and sealed in vials under vacuum. If aqueous ethanol is used in the extraction, ethanol is removed by distillation and the concentrated extract, after proper dilution with water, is freeze-dried. The content of GMG in the obtained solid is from 30% to 50% by weight, preferably 40% by weight.

GMG and GMG-ITC can be obtained in purified form by means of the procedure described in WO 2009/089889 A1.

According to said process, GMG is purified in two sequential steps by anion exchange and size exclusion chromatography and characterized by $^1$H and $^{13}$C NMR spectrometry. The purity is assayed by HPLC analysis of the desulfo-derivative yielding about 99% based on peak area value.

GMG-ITC is obtained by enzymatic conversion of GMG by using myrosinase isolated from seeds of *Sinapis alba* L. The total conversion of GMG into GMG-ITC is confirmed by HPLC analysis of the desulfo-derivative, which allows monitoring the reduction until complete disappearance of GMG in the reaction mixture. GMG-ITC is then purified (peak purity >99%) by reverse-phase chromatography, and analytically characterized by HPLC-DAD. Identification is then confirmed by means of $^1$H and $^{13}$C NMR.

GMG, GMG-ITC and a *Moringa oleifera* seeds extract containing GMG and/or GMG-ITC are able to modulate the peripheral neuropathic pain due to diabetes or induced by chemotherapy, in particular the peripheral neuropathic pain induced by chemotherapy with taxanes, platinum complexes such as cisplatin and oxaliplatin, epothilones, boronic acids such as bortezomid, *vinca* alkaloids such as vincristine.

According to the present invention, the *Moringa oleifera* seeds extract, GMG and GMG-ITC will be administered orally or topically, either alone or in combination with other substances with useful or complementary activity, formulated as tablets, capsules, granules, powders, syrups, ointment, gel and the like. The pharmaceutical formulations can be prepared with conventional procedures, using ingredients known in the technique, such as excipients, ligands, disintegrants, lubricants, stabilizing agents, and the like. Dosage may vary, according to the symptoms, weight of patients, severity of the disease and the like. A skilled practitioner will easily determine the most effective dosage regimen according to established methods. It is believed that the effective therapeutic doses in humans will range between 1 mg/Kg/die to 30 mg/Kg/die, even though higher dosages cannot be ruled out also in view of the limited toxicity of both GMG and GMG-ITC.

The invention is now further illustrated by the following example.

Biological Results

The acute oral effect of *Moringa oleifera* L. seeds extract and purified GMG and GMG-ITC on oxaliplatin induced hyperalgesia in mice (Cold plate test) were evaluated.

The method utilized is a modification of that described by Cavalletti et al. (Cavalletti G. et al., Eur. J. Cancer 37(18), 2457, 2001). Oxaliplatin (2.4 mg/kg) was dissolved in 5% glucose solution and administered i.p. for 5 consecutive days every week for 14 days. On day 14, the test products were suspended in 1% CMC and administered orally. Pregabalin was used, in the same experimental conditions, as a reference active compound at the dose of 15 mg/kg s.c. dissolved in saline.

Pain-related behavior (i.e. lifting and licking of the hind paw) were observed and the time (seconds) of the first sign was recorded.

The results are shown in Table.

TABLE

Acute oral effect of *Moringa oleifera* seed extract, GMG and GMG-ITC on oxaliplatin induced hyperalgesia in the mouse: Cold plate test

| | | | Licking latency (s) | | | |
|---|---|---|---|---|---|---|
| | | Pre-test | After Treatment with *Moringa oleifera* seed extract | | | |
| Treatment | Dose mg kg$^{-1}$ | (48 hrs after last oxaliplatin adm.) | 15 min | 30 min | 45 min | 60 min |
| vehicle + vehicle | | 19.9 ± 0.6 | 21.3 ± 0.5 | 21.9 ± 1.1 | 20.8 ± 0.6 | 21.4 ± 0.6 |
| oxaliplatin + vehicle | | 10.5 ± 0.4** | 11.1 ± 0.6** | 11.7 ± 1.0** | 10.2 ± 0.7** | 11.5 ± 0.9** |
| oxaliplatin + *Moringa oleifera* seeds extract | 100 | 11.0 ± 0.8** | 21.4 ± 1.2^^ | 17.8 ± 0.9^ | 16.1 ± 0.3^ | 10.9 ± 0.9 |
| oxaliplatin + GMG | 10 | 10.3 ± 0.5** | 21.1 ± 1.9^^ | 16.2 ± 0.7^ | 15.1 ± 1.3^ | 13.5 ± 2.3 |
| oxaliplatin + GMG-ITC | 10 | 10.2 ± 0.4** | 20.9 ± 1.8^^ | 16.0 ± 0.6^ | 15.0 ± 1.2^ | 13.3 ± 2.1 |
| Oxaliplatin + pregabalin (s.c.) | 15 | 11.0 ± 0.7** | 19.9 ± 1.9^ | 16.1 ± 0.6^ | 14.9 ± 1.3^ | 13.1 ± 2.0 |

**$P < 0.01$ vs vehicle + vehicle treated animals; ^$P < 0.05$ and ^^$P < 0.01$ vs oxaliplatin + vehicle treated animals. Each value represents the mean of 10 mice.

The results showed a significant activity of *Moringa oleifera* seeds extract and its purified major constituent on hyperalgesia induced by oxaliplatin in mouse. It is important to underline that this activity is comparable to that of pregabalin considered as the standard for this test.

The invention claimed is:

1. Method of treating oxaliplatin-induced neuropathy in a subject in need thereof, said method comprising
administering glucomoringin, or glucomoringin des-thio-glucoside, or an extract of *Moringa oleifera* seeds containing glucomoringin and/or glucomoringin des-thioglucoside to said subject; and treating said subject of said oxaliplatin-induced neuropathy.

2. A method according to claim 1, comprising administering glucomoringin.

3. A method according to claim 1, comprising administering glucomoringin des-thioglucoside.

* * * * *